United States Patent
Koch et al.

(10) Patent No.: US 10,071,008 B2
(45) Date of Patent: Sep. 11, 2018

(54) THERMOTHERAPY DEVICE

(71) Applicant: Dräger Medical GmbH, Lübeck (DE)

(72) Inventors: Jochim Koch, Ratzeburg (DE);
Markus Hampe, Lübeck (DE);
Claudia Kohnke, Lübeck (DE)

(73) Assignee: DRÄGERWERK AG & CO. KGAA, Lübeck (DE)

( * ) Notice: Subject to any disclaimer, the term of this patent is extended or adjusted under 35 U.S.C. 154(b) by 640 days.

(21) Appl. No.: 14/428,146

(22) PCT Filed: Sep. 2, 2013

(86) PCT No.: PCT/EP2013/068116
§ 371 (c)(1),
(2) Date: Mar. 13, 2015

(87) PCT Pub. No.: WO2014/040876
PCT Pub. Date: Mar. 20, 2014

(65) Prior Publication Data
US 2015/0257957 A1    Sep. 17, 2015

(30) Foreign Application Priority Data
Sep. 14, 2012   (DE) .......................... 10 2012 216 473

(51) Int. Cl.
*A61G 11/00* (2006.01)
*A61F 7/00* (2006.01)
*A61G 7/05* (2006.01)

(52) U.S. Cl.
CPC .............. *A61G 11/006* (2013.01); *A61F 7/00* (2013.01); *A61G 7/051* (2016.11)

(58) Field of Classification Search
CPC .......... A61G 11/006; A61G 7/051; A61F 7/00
(Continued)

(56) References Cited

U.S. PATENT DOCUMENTS

| 4,191,174 A | * | 3/1980 | Martin | ................... | A61G 11/00 |
| | | | | | 128/205.26 |
| 4,312,331 A | * | 1/1982 | Hahmann | ............. | A61G 11/00 |
| | | | | | 5/603 |

(Continued)

FOREIGN PATENT DOCUMENTS

| CA | 2273438 A1 | 1/2000 |
| CA | 2273438 C  | 5/2004 |

(Continued)

*Primary Examiner* — Navin Natnithithadha
*Assistant Examiner* — Sunita Reddy
(74) *Attorney, Agent, or Firm* — McGlew and Tuttle, P.C.

(57) ABSTRACT

A thermotherapy device (incubator) includes a lying surface bordered by side walls with a side wall part suspended via a hinge allowing downward pivoting with a lock for an upright closed position. The locking mechanism has a closing projection that can enter an open side receptacle, with guide curve, to lock the side wall part in the upright closed position on a stationary structure of the heat therapy device. The closing projection or the receptacle is suspended so as to be linearly movable in the direction of connection lines thereof to the pivot axis of the hinge, such that the closing projection can be moved to a position in front of the open side of the receptacle. A preloading apparatus ensures that the closing projection and the receptacle are pressed together in form-closed engagement when the closing projection and the open side of the receptacle are oriented toward each other.

14 Claims, 4 Drawing Sheets

(58) Field of Classification Search
USPC .................................................. 600/21–22
See application file for complete search history.

(56) References Cited

U.S. PATENT DOCUMENTS

| | | | |
|---|---|---|---|
| 5,112,293 A | | 5/1992 | Vaccaro |
| 5,980,449 A | * | 11/1999 | Benson ................ A47C 21/048 |
| | | | 600/22 |
| 6,231,499 B1 | | 5/2001 | Jones |
| 6,234,954 B1 | | 5/2001 | Mackin |
| 8,409,073 B2 | * | 4/2013 | Ibara ...................... A61G 11/00 |
| | | | 600/22 |
| 2002/0017248 A1 | * | 2/2002 | Honma .................. A61G 11/00 |
| | | | 119/311 |
| 2002/0019578 A1 | | 2/2002 | Honma et al. |
| 2002/0062523 A1 | * | 5/2002 | Prows .................... A61G 11/00 |
| | | | 5/658 |
| 2012/0269568 A1 | * | 10/2012 | Matsubara ........... A61G 11/006 |
| | | | 403/104 |

FOREIGN PATENT DOCUMENTS

| | | |
|---|---|---|
| CN | 2452484 Y | 10/2001 |
| DE | 600 27 388 T2 | 5/2007 |
| DE | 10 2006 046 466 B3 | 4/2008 |
| EP | 0749743 A2 | 12/1996 |
| EP | 2 514 399 A2 | 10/2012 |
| FR | 2473305 A1 | 7/1981 |
| GB | 2067077 A | 7/1981 |
| WO | 99/12511 A1 | 3/1999 |
| WO | 2009/073693 A1 | 6/2009 |

* cited by examiner

-- PRIOR ART --

THERMOTHERAPY DEVICE

CROSS REFERENCE TO RELATED APPLICATIONS

This application is a United States National Phase Application of International Application PCT/EP2013/068116 filed Sep. 2, 2013 and claims the benefit of priority under 35 U.S.C. § 119 of German Patent Application DE 10 2012 216 473.1 filed Sep. 14, 2012, the entire contents of which are incorporated herein by reference.

FIELD OF THE INVENTION

The present invention pertains to a thermotherapy device, especially an incubator, heating bed or open care unit, for the treatment of newborn babies with a reclining surface for accommodating a newborn baby, said reclining surface being bordered by side walls, wherein at least one side wall part is suspended by means of an associated hinge such that said at least one side wall part can be pivoted downwardly and a releasable locking mechanism for locking the side wall part in the upright closed position is present, which has a closing projection, a complementarily shaped receptacle, which is open on one side, and a guide curve, which is designed such that the closing projection can enter the receptacle through the open side for positive-locking meshing when the closed position of the side wall part is reached in order to thus lock the side wall part in the upright closed position on a stationary structure of the thermotherapy device.

BACKGROUND OF THE INVENTION

In many thermotherapy devices, the side walls can be open for better access to the infant. Thermotherapy devices with side walls that can be folded open are described, for example, in U.S. Pat. No. 6,231,499 B1 and WO 2009/073693 A1. In the closed position of the side walls, the latter must be held securely locked in order to prevent the patient from falling out. The standard IEC 60601-2-19 and -2-21 specifies corresponding requirements and tests for this. The closing mechanisms for holding the side walls in the closed position are not described more specifically in the above-mentioned two documents.

Simple snap closures, which snap in either at the upper edge of the side wall located next to it or on a side edge of the compartment (space accommodating the patient, for example, bordered by an incubator hood), are used for locking the side wall parts in the closed position in many currently used types of incubators with side wall parts that can be folded open. One closure each is present on each side of the side wall part for complete locking. However, two hands or at least two consecutive actuation steps with one hand are thus necessary for locking and unlocking. However, it would be desirable in respect to handling to have the ability to bring about opening by a single actuation step with one hand. In addition, this closing mechanism requires the presence of a fixed incubator hood or compartment, with which the side wall part can be locked.

In open care, in which no hood covering the patient space is normally used, it has become generally accepted to lock the side wall parts by a closing mechanism, which is integrated in the hinges with which the side wall parts are suspended such that they can be pivoted downward. The design of such a lockable hinge is schematically shown in FIG. 4. An edge of the reclining surface 16 of a thermo- therapy device, on which a side wall part 2 is suspended on the side by a hinge 3, is shown. The hinge 3 can be pivoted about a pivot axis 6 connected with the thermotherapy device. The pivot axis 6 is guided in a mount of the hinge, which mount has the cross section of an elongated hole. The hinge can therefore be raised and lowered with the side wall part when this side wall part is in the upright position, and the pivot axis 6 is displaced in the elongated hole mount in the process. The hinge is provided, further, with a pin 4, which can mesh with a groove connected rigidly with the thermotherapy device. By raising the sided wall part 2, the hinge is raised to the extent that the pin 4 separates from the groove upwardly, after which the side wall part 2 is freely pivotable. To close the side wall part, this is pivoted back. Shortly before the closed position is reached, the pin 4 comes into contact with a guide curve 5, which ensures that the hinge with the side wall part 2 is raised on it by the pin 4 sliding on the guide curve 5 to the extent that the pin 4 comes into a position above the groove, after which the side wall part 2 and the hinge 3 come into a lower position to the extent that the pin 4 is located in the groove and thus meshes with same, as a result of which the hinge 3 is blocked.

However, this kind of locking of the side wall part in the closed position is not optimal in terms of handling and generates mechanical jerks and jolts and closing noises when the pin is sliding over the edge of the guide curve, after which the entire side wall part and the hinge drop downward until the pin comes into contact with the bottom of the groove.

SUMMARY OF THE INVENTION

An object of the present invention is to design a thermotherapy device with side wall parts that can be folded away such that the locking of the side wall parts in the closed position can be carried out in a very simple manner in terms of handling and causes the least possible amount of shocks and noises.

According to the invention a thermotherapy device, especially an incubator, a heating bed or an open care unit, for the treatment of newborn babies, is provided with a reclining surface bordered by side walls for receiving a newborn baby. At least one side wall part is suspended with at least one associated hinge such that it can be pivoted downward. A releasable locking mechanism locks the side wall part in the upright closed position. The locking mechanism has a closing projection, a complementarily shaped receptacle, which is open on one side, and a guide curve, which is designed such that when the closed position of the side wall part is reached the projection can enter the receptacle through the open side of the receptacle, for positive-locking meshing in order to thus lock the side wall part in the upright closed position on a stationary structure of the thermotherapy device. The closing projection or receptacle is suspended linearly movably in the direction of connection lines with the pivot axis of the hinge, so that the closing projection can be moved into a position in front of the open side of the receptacle, and is provided with a prestressing device, which ensures that when the closing projection and the open side of the receptacle are oriented towards one another, the closing projection and the receptacle are pressed together into a positive-locking meshing (engaging) with one another.

Provisions are made according to the present invention for the closing projection or the receptacle to be suspended such that it is linearly movable in the direction of its connection line with the pivot axis of the hinge. The closing projection can be moved into a position in front of the open side of the receptacle. The prestressing device ensures that when the closing projection and the open side of the receptacle are oriented towards each other, the closing projection and the receptacle are pressed together in a positive-locking meshing.

It is possible, due to this design, to pivot the side wall part into the closed position with one hand, and the locking mechanism closes automatically by the closing projection coming to mesh with the receptacle.

Further, the side wall part performs a pure pivoting motion, without the side wall part being vertically lowered as a whole when the closed position is reached, as this happens in the state of the art forming this class. Only the closing projection or the receptacle is raised or lowered. This results in a reduced amount of shocks and disturbing noises, and the forces needed for operation are markedly lower. This is made ultimately possible by the vertical motion of the side wall parts as a whole being replaced by a relative motion of the closing projection and receptacle in relation to one another, so that the side wall part performs only a pure pivoting motion.

In a preferred embodiment, the locking mechanism has a lever, which is to be actuated manually and which acts on the movable component of the closing projection and receptacle in order to move the closing projection and the receptacle relative to one another and to release the meshing of these parts as a result, so that the side wall part can be pivoted downward. As a result, the side wall can also be opened without raising it completely.

The closing projection can be suspended on the side wall part and the receptacle on a stationary structure of the thermotherapy device or vice versa. Further, the closing projection may be suspended movably, while the receptacle is arranged stationarily, or vice versa. These different design possibilities are described. In principle, both the closing projection and the receptacle may be suspended such that they are linearly movable as long as the guide curve ensures that the closing projection is located in front of the open side of the receptacle during the motion of the closing projection into the closed position, so that the prestressing device can then press the two components together into a meshing position.

The present invention will be explained below on the basis of an exemplary embodiment shown in the drawings. The present invention shall be explained in more detail on the basis of the following figures and exemplary embodiments, without the present invention being limited to these. The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
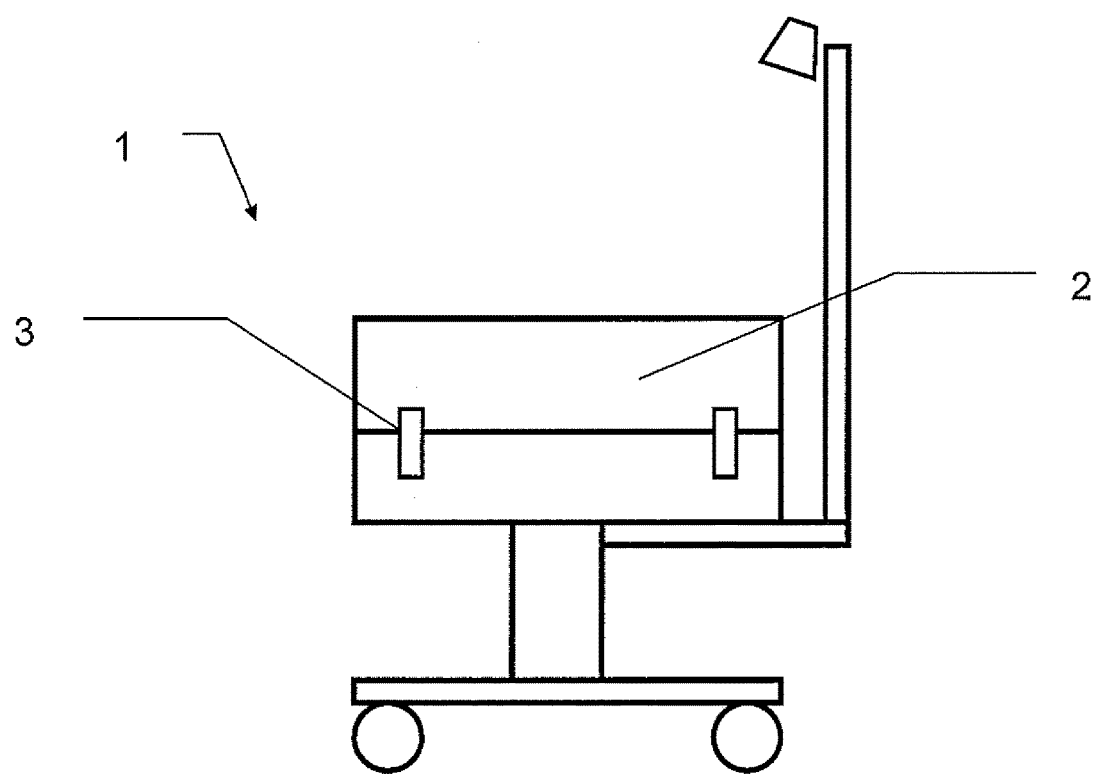
FIG. 1 is a schematic side view of a thermotherapy device.

Referring to the drawings, FIG. 1 shows a schematic side view of a thermotherapy device 1. The thermotherapy device 1 has a therapy unit on a chassis and a radiant heater suspended on a carrier column. The therapy unit comprises a reclining surface bordered by side walls. A side wall part 2 is suspended pivotably with hinges 3, so that it can be pivoted from an upright closed position into a downwardly folded-away position.

Figure 2:
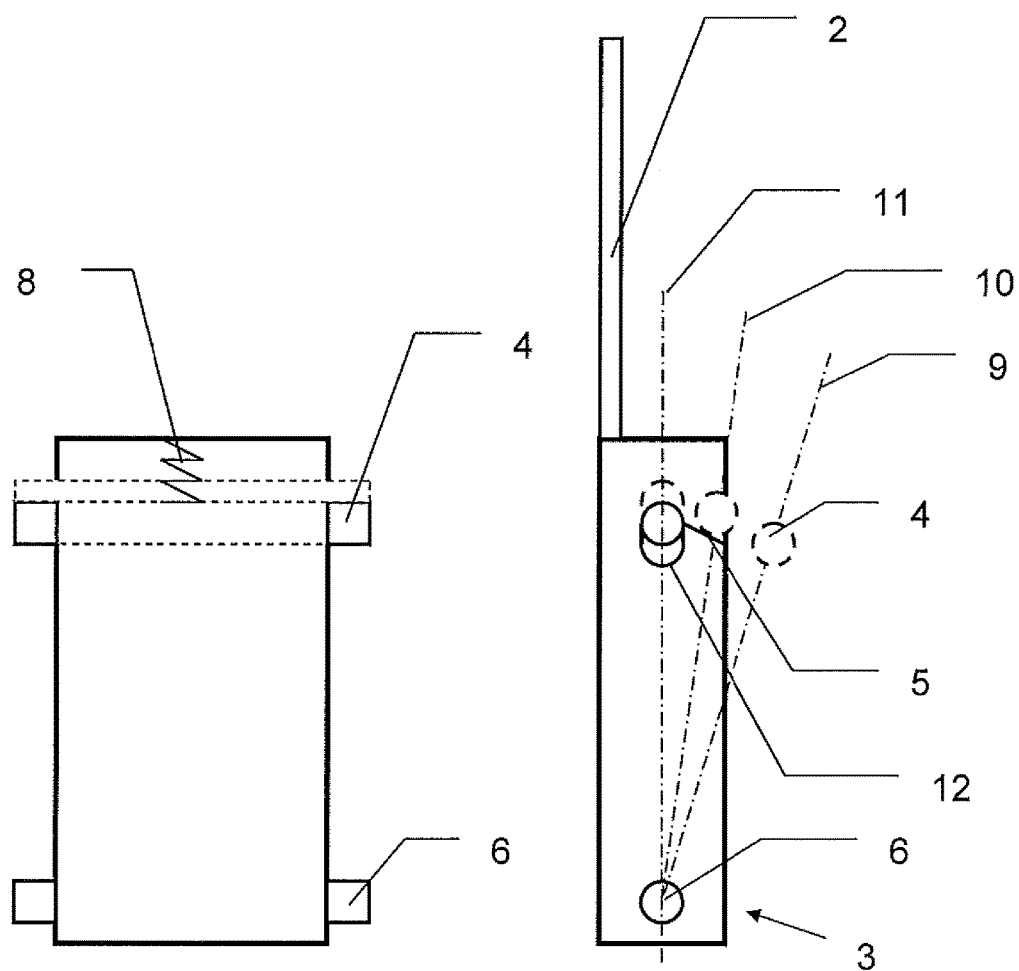
FIG. 2 is a top and side schematic view of a locking mechanism for a thermotherapy device according to the present invention.

FIG. 2 shows a side wall part 2 with hinge 3 and a locking mechanism in a front view and in a side view. The hinge 3 is suspended on a pivot axis 6, which is rigidly connected with the thermotherapy device. The locking mechanism comprises a closing projection 4 connected with the hinge in the form of a pin, wherein the pin 4 is suspended such that it is linearly movable in the direction of the connection line between the pin 4 and the pivot axis 6. Further, a receptacle 12 stationarily connected with the thermotherapy device in the form of a groove is present. The groove is adjoined by a guide curve 5, which is stationary in relation to the receptacle 12. When the side wall part 2 is brought again from its open, folded-away position into the closed position, the hinge 3 passes through the positions indicated by the broken lines 9, 10 and 11 while approaching the closed position. In position 9, the pin 4 is still moving freely and is pivoted with the hinge 3. When the pin 4 comes into contact with the guide curve 5, the pin 4 is now pushed against the prestressing of a prestressing device 8 to a greater distance from the pivot axis 6, essentially in the upward direction. When the hinge 3 has reached the upright closed position indicated by the broken line 11, the pin 4 is aligned with the open side of the receptacle 12. When this position is reached, the pin 4 is then pressed by the prestressing device 8 into the receptacle 12, because it has left the guide curve 5.

To open the side wall part 2 shown in FIG. 2, the pin 4 must be released from the receptacle 12. To do so, the pin must be raised manually against the prestressing, for example, by applying an upwardly directed force manually on a projecting area of the pin. It would also be possible, in principle, to mount the hinge with an elongated hole on the pivot axis 6, differently from what is shown in FIG. 2, so that the hinge as a whole can be raised in order to raise the pin out of the receptacle 12. However, a purely pivotable mounting of the hinge 3 is preferred, because raising of the side wall part 2 is also avoided now when opening the side wall part. The raising of the pin 4 out of the receptacle 12, which is then necessary for opening the side wall part 2, can be performed in a simple manner especially in the embodiment variant according to FIG. 3.

Figure 3:
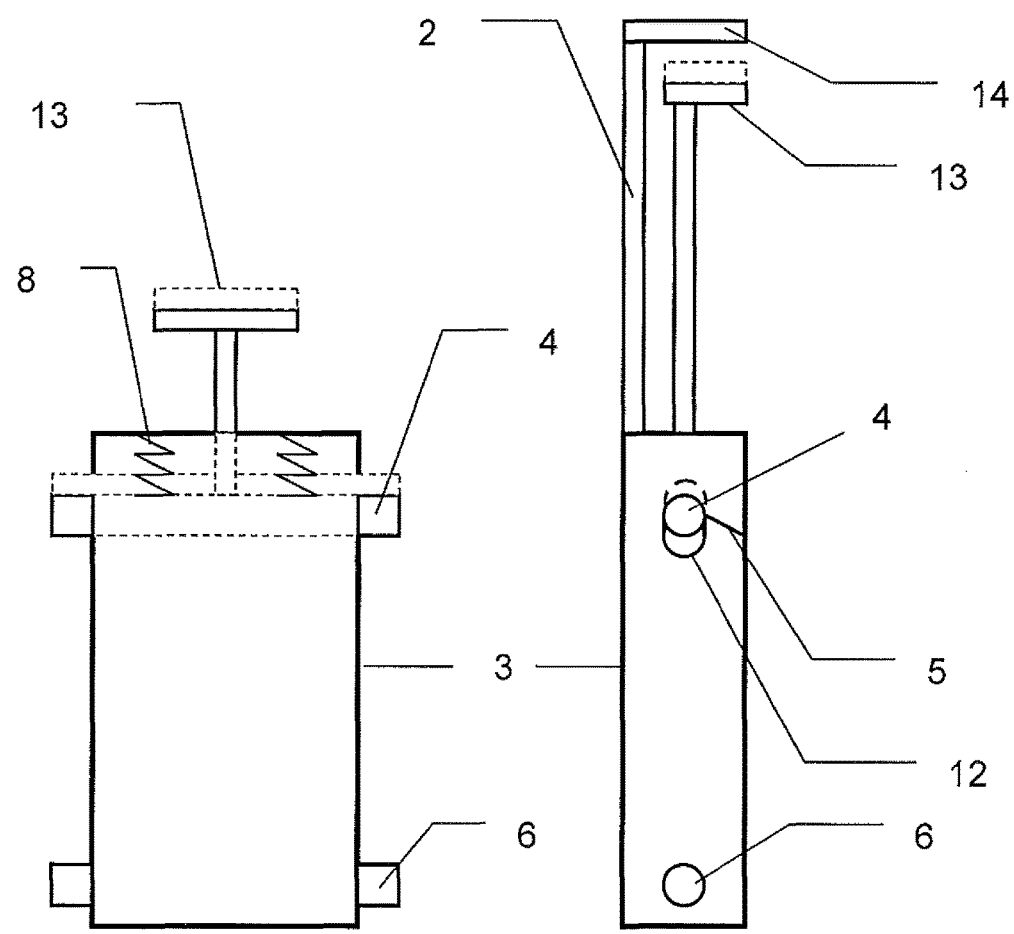
FIG. 3 is a top and side schematic view of a preferred locking mechanism for a thermotherapy device according to the present invention.
Figure 4:
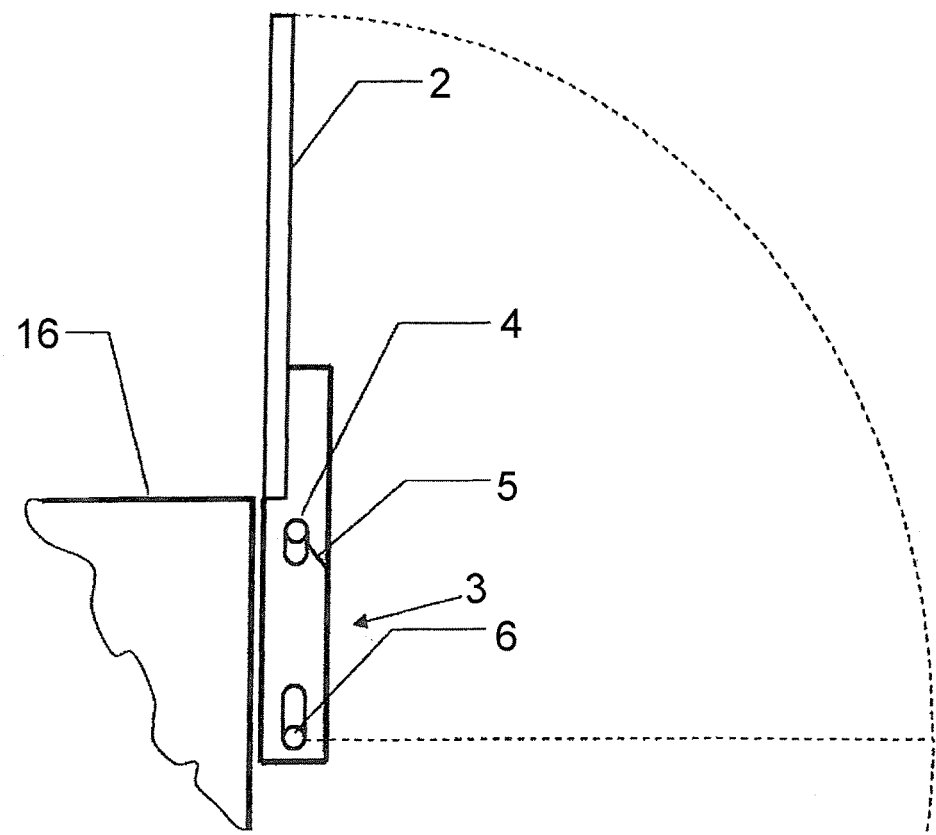
FIG. 4 is a detail view of a thermotherapy device with a locking mechanism for a side wall part according to the state of the art.

FIG. 3 shows a variant of the side wall parts 2 for a thermotherapy device according to the present invention with a top view of the hinge and a side view of the hinge and locking mechanism. The hinge 3 is shown in the side view in the locked position with the pin 4 meshing with the receptacle 12. The hinge 3 is provided here with a lever 13, which can be displaced in the vertical direction and which can be displaced from the position shown in FIG. 3 into a raised position indicated by broken lines. The lever 13 is connected with the pin 4 in such a way that when raising the lever 13, the pin 4 is raised as well, which is represented by the contour of the pin indicated by broken lines. In its raised position, the pin 4 is raised out of the receptacle 12 to the extent that it can be moved over the edge of the guide curve 5 facing the receptacle 12. The locking mechanism can consequently be opened by the user pulling the lever 13 in the direction of a counterpiece 14, e.g., by placing his thumb on the counterpiece 14 and pulling up the lever with the other fingers. After tightening the lever 13, the side wall part 2 can be pivoted downward about the pivot axis 6 with the hinge 3. When pivoting back into the closed position, the pin 4 slides onto the guide curve 5 when the outer end of said guide curve 5 is reached and is then raised from this guide curve against the prestressing device 8 during further pivoting over the guide curve, so that when the end position is reached, it leaves the outer edge of the guide curve 5 above the open sides of the receptacle 12, after which the movable pin is pressed into the receptacle 12 and brings about locking of the hinge 3 as a result.

It would also be possible, in principle, to hold a side wall part 2 by a magnet closure in the closed position. One magnet would be arranged for this on the pivotable hinge and one magnet on the stationary structure of the thermotherapy device such that the magnets are directed towards one another with opposite pole orientations in the closed position of the side wall part, so that the hinge is held in the closed position by the magnets facing one another. After applying a minimum force, which is determined by the strength and arrangement of the magnets in relation to one another, the hinge with the side wall part on it can be pivoted from the closed position into the open, folded-away position.

While specific embodiments of the invention have been shown and described in detail to illustrate the application of the principles of the invention, it will be understood that the invention may be embodied otherwise without departing from such principles.

The invention claimed is:

1. A thermotherapy device comprising:
   a reclining surface;
   side walls, bordering the reclining surface, the reclining surface being configured for receiving a newborn baby, wherein the sidewalls comprise at least one side wall part, the at least one side wall part comprising an upright closed position;
   a hinge, the at least one side wall part being suspended with the hinge for pivoting the at least one side wall part downward about a pivot axis; and
   a releasable locking mechanism configured to lock the side wall part in the upright closed position, said locking mechanism comprising a closing projection, a complementarily shaped receptacle, which is open on one side, and a guide curve, wherein the closing projection enters the receptacle through the open side of the receptacle for positive-locking meshing to lock the side wall part in the upright closed position on a stationary structure of the thermotherapy device, one of the closing projection and the receptacle being suspended linearly movably in a direction of the pivot axis of the hinge into a position in front of the open side of the receptacle, and
   a prestressing device pressing, with the closing projection and the open side of the receptacle oriented towards one another, the closing projection and the receptacle together into a positive-locking meshing with one another.

2. The thermotherapy device in accordance with claim 1, wherein the locking mechanism has a lever, which acts on a movable component of the closing projection and receptacle during actuation to release the positive-locking meshing of the closing projection and receptacle, wherein the side wall part is pivoted downward upon release of the positive-locking meshing of the closing projection and receptacle.

3. The thermotherapy device in accordance with claim 1, wherein the closing projection is suspended linearly movably on the side wall part and the receptacle is arranged stationarily on the stationary structure of the thermotherapy device.

4. The thermotherapy device in accordance with claim 3, wherein the receptacle is upwardly open, the guide curve pressing the closing projection upwardly against a force of the prestressing device before the receptacle is reached, and the prestressing device being configured to press the closing projection downwardly into the receptacle upon the closing projection reaching the upwardly open receptacle.

5. The thermotherapy device in accordance with claim 3, wherein the receptacle is downwardly open, the guide curve pressing the closing projection downward against a force of the prestressing device before the receptacle is reached, and the prestressing device being configured to press the closing projection upward into the receptacle upon the closing projection reaching the receptacle.

6. The thermotherapy device in accordance with claim 1, wherein the closing projection is arranged rigidly on the side wall part and the receptacle is arranged linearly movably on the stationary structure of the thermotherapy device.

7. The thermotherapy device in accordance with claim 6, wherein the receptacle is upwardly open, the guide curve pressing the receptacle downward against a force of the prestressing device before the closing projection reaches the guide curve, and the prestressing device being configured to press the receptacle upward to mesh with the closing projection upon the closing projection reaching the receptacle.

8. The thermotherapy device in accordance with claim 6, wherein the receptacle is downwardly open, the guide curve pressing the receptacle, before the closing projection reaches the receptacle, upwardly against a force of the prestressing device, and the prestressing device pressing the receptacle, before the closing projection reaches the receptacle, downwardly against the closing projection.

9. The thermotherapy device in accordance with claim 1, wherein the receptacle is suspended linearly movably on the side wall part and the closing projection is arranged rigidly on the stationary structure of the thermotherapy device.

10. The thermotherapy device in accordance with claim 9, wherein the receptacle is upwardly open, the guide curve presses the receptacle against a force of the prestressing device before the closing projection is reached, and the prestressing device being configured to press the receptacle upwardly against the closing projection upon the receptacle reaching the closing projection.

11. The thermotherapy device in accordance with claim 9, wherein the receptacle is downwardly open, the guide curve pressing the receptacle upwardly against a force of the prestressing device before the closing projection is reached, and the prestressing device being configured to press the receptacle downwardly against the closing projection upon the receptacle reaching the closing projection.

12. The thermotherapy device in accordance with claim 1, wherein the receptacle is arranged rigidly on the side wall part and the closing projection is arranged linearly movably on the stationary structure of the thermotherapy device.

13. The thermotherapy device in accordance with claim 12, wherein the receptacle is upwardly open, the guide curve pressing the closing projection, before the receptacle reaches the closing projection, upwardly against a force of the prestressing device, and the prestressing device being configured to press the closing projection downwardly into the receptacle upon the receptacle reaching the closing projection.

14. The thermotherapy device in accordance with claim 12, wherein the receptacle is downwardly open, the guide curve pressing the closing projection, before the receptacle reaches the closing projection, downwardly against a force of the prestressing device, and the prestressing device being configured to press the closing projection upwardly into the receptacle upon the receptacle reaches the closing projection.

* * * * *